United States Patent [19]

Hamilton, Jr. et al.

[11] Patent Number: 4,956,516

[45] Date of Patent: * Sep. 11, 1990

[54] DISPROPORTIONATION OF OLEFINS

[75] Inventors: David M. Hamilton, Jr.; Richard A. Kemp, both of Houston, Tex.

[73] Assignee: Shell Oil Company, Houston, Tex.

[*] Notice: The portion of the term of this patent subsequent to Jun. 28, 2005 has been disclaimed.

[21] Appl. No.: 196,576

[22] Filed: May 20, 1988

[51] Int. Cl.$^5$ .............................................. C07C 6/00
[52] U.S. Cl. ................................. 585/646; 585/643; 502/210; 502/211; 502/213
[58] Field of Search ................. 585/646, 643; 502/210, 502/211, 213

[56] References Cited

U.S. PATENT DOCUMENTS

| | | | |
|---|---|---|---|
| 3,261,879 | 7/1966 | Banks | 260/683 |
| 3,296,330 | 1/1967 | Sherk | 585/646 |
| 3,340,322 | 9/1967 | Heckelsberg | 260/683 |
| 3,346,661 | 10/1967 | Wilson et al. | 260/683 |
| 3,511,890 | 5/1970 | Reusser | 585/646 |
| 3,574,779 | 4/1971 | Lester et al. | 260/676 |
| 3,637,892 | 1/1972 | McGrath et al. | 260/683 D |
| 3,637,893 | 1/1972 | Singleton | 260/683 D |
| 3,725,496 | 4/1973 | Kobylinski et al. | 260/683 D |
| 3,760,026 | 9/1973 | Reusser et al. | 260/683 D |
| 3,773,845 | 11/1973 | Hughes | 260/676 R |
| 3,792,108 | 2/1974 | Arganbright | 260/683 D |
| 3,855,340 | 12/1974 | Knoche | 260/683 D |
| 3,856,876 | 12/1974 | Burnett | 260/676 R |
| 3,872,180 | 3/1975 | Nakatomi et al. | 260/683 D |
| 3,888,940 | 6/1975 | Kubicek | 260/683 D |
| 3,996,166 | 12/1976 | Banks et al. | 252/437 |
| 4,098,839 | 7/1978 | Wilms et al. | 260/683.15 |
| 4,276,199 | 6/1981 | Hoxmeier | 252/438 |
| 4,368,141 | 1/1983 | Kukes | 252/439 |
| 4,487,986 | 12/1984 | Kukes | 585/645 |
| 4,517,401 | 5/1985 | Kukes et al. | 585/645 |
| 4,522,936 | 6/1985 | Kukes et al. | 502/249 |
| 4,524,235 | 6/1985 | Banks et al. | 585/646 |
| 4,624,938 | 11/1986 | Kemp | 585/646 |
| 4,629,716 | 12/1986 | Kemp | 502/208 |
| 4,629,717 | 12/1986 | Chao | 502/208 |
| 4,754,099 | 6/1988 | Kemp et al. | 585/646 |

FOREIGN PATENT DOCUMENTS

| | | | |
|---|---|---|---|
| 847420 | 2/1977 | Belgium . | |
| 802268 | 12/1968 | Canada . | |
| 2526035 | 12/1976 | Fed. Rep. of Germany . | |
| 7322683 | 7/1973 | Japan . | |
| 9007203 | 1/1974 | Japan . | |
| 50-24283 | 8/1975 | Japan . | |
| 6514985 | 5/1966 | Netherlands . | |
| 7011180 | 10/1970 | Netherlands . | |
| 7111880 | 5/1972 | Netherlands . | |
| 7204822 | 10/1972 | Netherlands . | |
| 978907 | 12/1982 | U.S.S.R. . | |
| 972935 | 10/1964 | United Kingdom | 585/646 |
| 1128091 | 9/1968 | United Kingdom . | |

*Primary Examiner*—Chung K. Pak
*Attorney, Agent, or Firm*—Pamela J. McCollough

[57] ABSTRACT

This invention relates to a process for disproportionation of hydrocarbon olefins by contacting said hydrocarbon at disproportionation conditions with a catalyst prepared by incorporating a metals solution containing cobalt and an element selected from the group consisting of molybdenum, tungsten and mixtures thereof, and a phosphorus-containing compound into an alumina hydrogel. The final calcined catalysts have surface areas greater than about 225 m$^2$/g and more than about 50% of their pore volume in pores having diameters less than about 70 Å.

52 Claims, No Drawings

DISPROPORTIONATION OF OLEFINS

FIELD OF THE INVENTION

This invention relates to a process for the disproportionation of olefinic hydrocarbons utilizing a hydrogel-derived catalyst.

BACKGROUND OF THE INVENTION

Reactions of olefinic molecules in the presence of metal-containing catalysts to produce other olefinic molecules are known in the art as "disproportionation" reactions. A typical olefin disproportionation process is illustrated by U.S. Pat. No. 3,261,879, issued Jul. 19, 1966, to Banks, wherein two similar non-symmetrical molecules of an olefin react in the presence of certain catalysts to produce one olefin of a higher carbon number and one olefin of a lower carbon number such as, for example, propylene disproportionation by the process of U.S. Pat. No. 3,261,879 to produce ethylene and butylenes.

A variation of this disproportionation process, which might be termed "reverse disproportionation", is illustrated by the Netherlands Patent Application 6514985 of British Petroleum Company, Limited, published May 20, 1966, wherein, in one modification, molecules of two dissimilar symmetrical olefins are reacted to form two molecules of a single olefin product, e.g., ethylene and 2-butene react to form proplyene.

Another variation of the process, being conveniently termed "ring opening disproportionation" to distinguish it from other variations, is disclosed by British Patent Specification No. 1,163,657 of Phillips Petroleum Company, published Sept. 10, 1969, wherein a cyclic olefin and an acyclic olefin react to form a single product molecule. For example, ethylene reacts with cyclopentene by ring opening disproportionation to produce 1,6-heptadiene.

As used in this application, disproportionation process means the conversion of olefinic hydrocarbons into similar olefinic hydrocarbons of higher and lower numbers of carbon atoms per molecule. Where the reactant comprises 1- or 2-olefins having relatively long chains, a mixture of products is obtained comprising primarily olefins having both a larger and a smaller number of carbon atoms than the feed olefin but also including other disproportionated products, for example, saturated hydrocarbons, and other converted and unconverted material. Such an operation is useful in many instances. For example, a more plentiful hydrocarbon can be converted to a less plentiful and therefore more valuable hydrocarbon. One instance of such a conversion occurs when the process of this invention is used to convert both higher and lower molecular weight olefins to olefins in the $C_{10}$–$C_{16}$ range, a range of olefins especially suitable for the manufacture of detergents. Another instance of a disproportionation reaction having considerable value is the disproportionation of propylene to produce ethylene and butene.

A variety of catalysts have been employed for conducting disproportionation reactions, such as those disclosed in U.S. Pat. No. 3,340,322, issued Sept. 5, 1967; U.S. Pat. No. 3.637,892, issued Jan. 25, 1972; U.S. Pat. No. 3,760,026, issued Sept. 18, 1973; U.S. Pat. No. 3,792,108, issued Feb. 12, 1974; U.S. Pat. No. 3,872,180, issued Mar. 18, 1975; and British Patent Specification No. 1,128,091, published Mar. 16, 1966.

The catalysts in the above references are generally prepared according to conventional methods such as impregnation, wherein a carrier is impregnated with a solution of metals; co-precipitation, wherein a carrier compound and metals are simultaneously precipitated; or co-mulling, wherein dry powders are mixed with a suitable extrusion aid such as water and extruded.

A related case directed to the disproportionation of olefins using a hydrogel-derived catalyst is commonly-assigned copending application Ser. No. 056,185, filed May 27, 1985, now U.S. Pat. No. 4,754,099.

SUMMARY OF THE INVENTION

The present invention relates to a process for the disproportionation of olefinic hydrocarbons which comprises contacting said olefinic hydrocarbons with a catalyst comprising cobalt, an element selected from the group consisting of molybdenum, tungsten and mixtures thereof, and a phosphorus-containing compound incorporated into an alumina hydrogen which is then processed to prepare the catalyst.

It has been found that a hydrogen-derived catalyst has improved activity in an olefin disproportionation process when compared to a conventionally prepared catalyst useful for disproportionation. The hydrogel-derived catalyst in this invention can be prepared by adding catalytically active metals to an alumina hydrogel as dry salts, solutions, or a mixture of dry salts and solutions. As used herein, the term "salts" includes compounds and complexes. In an olefin production process combining the steps of oligomerization, isomerization and disproportionation such as that disclosed in U.S. Pat. No. 3,726,938, issued to Berger, it is preferred to use catalysts prepared according to the instant invention in the disproportionation zone. Another advantage of the hydrogel route is a lower manufacturing cost due to reduced product yield loss and reduced number of heating steps. The catalysts prepared according to the invention have high surface areas, greater than about 225 $m^2/g$, and substantial portions, greater than about 50%, of their pore volume in pores having diameters less than about 70 Å.

DESCRIPTION OF THE PREFERRED EMBODIMENTS

In the process of the instant invention, the disproportionation of an olefinic hydrocarbon is accomplished by contacting the olefinic hydrocarbon with a catalyst prepared by incorporating cobalt, an element selected from the group consisting of molybdenum, tungsten and mixtures thereof, and a phosphorus-containing compound into an alumina hydrogel and subsequently processing the hydrogel to prepare the catalyst.

Olefins which are subjected to disproportionation according to the process of this invention include $C_3+$ olefinic hydrocarbons or $C_3+$ internal olefins in combination with ethylene. A useful group of feed materials are olefinic hydrocarbons having carbon numbers ranging from $C_2$ to about $C_{100}$ and mixtures thereof, preferably from $C_2$ to about $C_{60}$ and mixtures thereof, and more preferably linear olefinic hydrocarbons having carbon numbers ranging from about $C_4$ to about $C_{40}$ and mixtures thereof. Examples of compounds most suitable for disproportionation according to this invention are acyclic 1- and 2-alkenes, and alkyl and aryl derivatives thereof having from 3 to 20 carbon atoms per molecule. Some specific examples of such olefins are propylene, 1-butene, 2-butene, 1-pentene, 2-pentene, 1-hexene, 2- heptene, 1-octene, 2-nonene, 1-dodecene, 2-tetradecene, 1-hexadecene, 2-methyl-1-butene, 2-methyl-2-butene, 3methyl-1-butene, 1-phenyl-2-butene, and 3-heptene. Higher disproportionation conversions and wider product distributions are obtained at comparable reaction times with 1-olefins than with 2-olefins. 3-olefins are disproportionated at still lower rates.

The feed should be essentially free of impurities which adversely affect the reaction. A subsequent reactivation of the catalyst to remove the effect of such impurities can be made repeatedly by heat treatment with air, using an inert gas to control burn-off temperature.

The catalyst of this invention is prepared by incorporating cobalt, an element selected from the group consisting of molybdenum, tungsten and mixtures thereof, and a phosphorus-containing compound into an alumina hydrogel having a water content sufficient to provide a hdyrogen which is thixotropic, and subsequently calcining to prepare the catalyst.

As used herein, the phrase "hydrogel which is thixotropic" refers to an alumina hydrogel which becomes a fluid when it is subjected to an external force such as mixing, shaking, milling, shearing and the like. The amount of water which must be present in the hydrogel in order to obtain a hydrogel which is thixotropic can be readily determined by one of ordinary skill in the art with a minimal amount of experimentation. In general, the hydrogel has a water content greater than about 70%, basis dry weight of alumina. In a preferred embodiment, the hydrogel has a water content in the range of from about 70% to about 95%, preferably from about 75% to about 90%, basis dry weight of alumina.

The catalysts used in this invention are prepared by the preparative techniques disclosed in the following commonly-assigned, copending applications which are directed to hydrotreating: Ser. No. 100,662, filed Sept. 24, 1987; Ser. No. 100,663, filed Sept. 24, 1987 and Ser. No. 100,661, filed Sept. 24, 1987; and in the following U.S. patents directed to hydrotreating: U.S. Pat. No. 4,717,698, U.S. Pat. No. 4,717,704 and U.S. Pat. No. 4,717,705, which are incorporated by reference herein.

The alumina hydrogel is typically prepared by titrating an aqueous solution of one or more aluminum salt(s) with an appropriate acidic or basic material or solution, optionally in the presence of a phosphorus-containing compound, to cause precipitation of the alumina gel. One skilled in the art will recognize that the alumina gel can be prepared by titrating an acidic aluminum salt such as, for example, aluminum sulfate, aluminum nitrate or aluminum chloride, in aqueous solution with a basic precipitating medium such as, for example, sodium hydroxide or ammonium hydroxide, optionally in the presence of a phosphorus-containing compound, or, by titrating an alkali metal aluminate such as, for example, sodium aluminate or potassium aluminate, in aqueous solution with an acidic precipitating medium such as, for example, hydrochloric acid or nitric acid, optionally in the presence of a phosphorus-containing compound. One skilled in the art will recognize that the adjustment of the pH of an aluminum-containing solution to between about 5.5 and about 10.0 will result in precipitation of the aluminum as aluminum hydroxide or hydrated aluminum oxide.

As used herein, the term "a phosphorus-containing compound" is generic and refers to one phosphorus-containing compound as well as to more than one phosphorus-containing compound. Suitable phosphorus-containing compounds are the acids of phosphorus and their salts. Typical acids of phosphorus include phosphonic acids, phosphinic acids, phosphorus acids and the like. The phosphorus-containing compound is generally selected from the group consisting of phosphoric acid, a phosphate salt and mixtures thereof. Suitable phosphate salts include alkali metal phosphates, alkali metal hydrogen phosphates, ammonium phosphate and ammonium hdyrogen phosphate. The phosphorus-containing compound is preferably phosphoric acid and is preferably mixed with the acid aluminum species prior to the precipitation. Alternatively, the phosphorus-containing compound can be sodium or ammonium phosphate and mixed with the basic aluminum species prior to precipitation. The phosphorus-containing compound can also be added as a separate solution or added to both the acid aluminum species and the basic aluminum species without significantly affecting the results. Preferably, the phosphorus-containing compound is prepared using commercially available 85% phosphoric acid although other phosphorus-containing materials may be utilized. The amount of phosphorus-containing compound added to the acid aluminum species and/or the basic aluminum species is from about 0.02 to about 0.60 moles of phosphorus per mole of aluminum.

In a preferred embodiment, the alumina hydrogel is prepared by titrating an aqueous solution of an alkali metal aluminate and an aqueous solution of an acid aluminum salt to cause precipitation of the alumina gel. Suitable acidic aluminum salts include aluminum sulfate, aluminum nitrate and aluminum chloride. A preferred species is aluminum chloride. Suitable alkali metal aluminates are sodium aluminate and potassium aluminate. The precipitation can be carried out by adding an aqueous solution to the basic aluminum species to an aqueous solution of the acidic aluminum species or the procedure can be reversed by adding an aqueous solution of the acidic aluminum species to an aqueous solution of the basic aluminum species (referred to as "sequential precipitation"). Preferably, the precipitation in the instant invention is carried out by simultaneously adding the acid aluminum species and the basic aluminum species to cause precipitation of the hydrogel (referred to as "simultaneous precipitation"). The maximum rate of addition of the acid aluminum species and the basic aluminum species is fixed by the rate at which the two streams can be mixed and the pH and temperature of the system can be effectively controlled.

The ranges and limitations provided in the instant specification and claims are those which are believed to particularly point out and distinctly claim the instant invention. It is, however, understood that other ranges and limitations that perform substantially the same function in substantially the same manner to obtain the same result are intended to be within the scope of the instant invention as defined by the instant specification and claims.

The temperature and pH of the precipitation are important variables in the preparation of the aluminas into which metals can be incorporated to form catalysts with desirable physical qualities. One skilled in the art would recognize that changes in precipitation temperatures and pHs result in changes in porosities. The optimal temperatures and pHs for the precipitation of the aluminas can be determined with a minimal amount of routine experimentation. In the instant invention, a precipitation temperature typically ranges from about 20° C. to about 90° C., preferably from about 50° C. to about 85°

C., more preferably from about 55° C. to about 65° C., and a precipitation pH typically ranges between about 5.5 and about 10.0, preferably between about 5.5 and about 8.0, and more preferably between about 6.0 and about 7.5. The length of time required for the precipitation step is typically from about 15 minutes to about 45 minutes. The period of time for the precipitation should be sufficiently long for adequate mixing of the materials, but not long enough for enhanced particle growth to occur.

After the precipitation step is completed, the pH of the slurry is adjusted by the addition of the basic aluminate solution to fall in the range from about 8.0 to about 12.0, preferably about 9.0 to about 11.0, most preferably about 9.5 to about 10.5, and aged at a temperature in the range from about 20° C. to about 90° C., preferably about 50° C. to about 85° C. for at least 15 minutes. An upper limit on the length of time for aging is not critical and is normally determined by economical considerations. Aging times will typically range from about 0.1 to about 10 hours, preferably from about 0.25 to about 5 hours, and more preferably from about 0.25 to about 1 hour. In general, aluminas with acceptable properties are produced by holding the aging temperature equal to the precipitation temperature.

After aging, the slurry is washed and filtered in routine fashion to remove substantially all of the water-soluble salts formed during the precipitation of the hydrogel. The preferred solvent for washing is water although other solvents such as lower alkanols may be utilized.

After washing, the metals are incorporated into the hydrogel. One method for adding the metals to the hydrogel is a reslurry step in which the hydrogel is reslurried with a metals solution containing solubilized salts of cobalt, an element selected from the group consisting of molybdenum, tungsten and mixtures thereof, and a phosphorus-containing compound sufficient to deposit on the final catalyst from about 0.1% w to about 5% w cobalt, from about 5% w to about 18% w molybdenum or about 8% w to about 32% w tungsten, and from about 1% w to about 6% w phosphorus. When mixtures of molybdenum and tungsten are utilized, the final catalyst contains from about 5% w to about 32% w molybdenum and tungsten. The solotion may, however, contain amounts of cobalt and molybdenum or tungsten in excess of that required to deposit the aforesaid amounts of metals, which excess may be removed by washing or other techniques following the reslurry step. A typical metals solution can be prepared by combining a molybdenum solution with a cobalt solution. The metals solution also contains a stabilizing amount of phosphorus. Typically, the metals solution contains an amount of phosphorus-containing compound in the range from about 0.17 to about 7.1 moles of phosphorus per mole of molybdenum or tungsten. When a phosphorus-containing compound is added to the acidic or basic species during precipitation of the hydrogel, the amount of phosphorus-containing compound added to the metals solution is adjusted to give a final calcined catalyst containing from about 1% w to about 6% w phosphorus. Suitable phosphorus-containing compounds are the acids of phosphorus and their salts. Typical acids of phosphorus include phosphoric acids, phosphonic acids, phosphinic acids, phosphorus acids and the like. The phosphorus-containing compound is generally selected from the group consisting of phosphoric acid, a phosphate salt and mixtures thereof. Suitable phosphate salts include alkali metal phosphates, alkali metal hydrogen phosphates, ammonium phosphate and ammonium hydrogen phosphate.

The molybdenum solution consists of a water-soluble source of molybdenum oxide such as ammonium heptamolybdate or ammonium dimolybdate dissolved in water and optionally, a phosphorus-containing compound. Hydrogen peroxide may also be used to aid in solution preparation in some cases. A preferred method for preparing the molybdenum solution consists of adding hydrogen peroxide to the solution in an amount ranging from about 0.1 to about 1.0 mole of hydrogen peroxide per mole of molybdenum. Optionally, a suitable soluble amine compound such as monoethanolamine, propanolamine or ethylenediamine may be added to the molybdenum solution in order to aid in stabilization of the solution.

The tungsten solution typically consists of ammonium metatungstate dissolved in water and optionally, a phosphorus-containing compound. A preferred method for preparing the tungsten solution consists of adding hydrogen peroxide to the solution in an amount ranging from about 0.1 to about 1.0 mole of hydrogen peroxide per mole of tungsten. In addition, a suitable soluble amine compound such as monoethanolamine, propanolamine or ethylenediamine may be added to the tungsten solution in order to aid in stabilization of the solution.

The cobalt solution consists of cobalt salts dissolved in water and optionally, a phosphorus-containing compound. A wide range of cobalt compounds are suitable, such as cobalt nitrate, cobalt hydroxide, cobalt acetate, cobalt oxalate, or cobalt oxide. The preferred cobalt compound is cobalt nitrate.

An alternative method for incorporating the metals into the hydrogel is to add dry, water-soluble metal salts of cobalt, a heavy metal selected from the group consisting of molybdenum, tungsten and mixtures thereof, and a phosphorus-containing compound to the hydrogel and mix until dissolution and adsorption of the metal salts and the phosphorus-containing compound onto the gel is substantially complete. The metal salts of cobalt, molybdenum and/or tungsten and phosphorus-containing compound are added to the hydrogel in amounts sufficient to incorporate into the final catalyst from about 0.1% w to about 5% w cobalt, from about 5% w to about 18% w molybdenum or about 8% w to about 32% w tungsten and from about 1% w to about 6% w phosphorus. When mixtures of molybdenum and tungsten are utilized, the final catalyst contains about 5% w to about 32% w molybdenum and tungsten.

Molybdenum is generally added to the hydrogel as a dry, water-soluble source of molybdenum such as ammonium heptamolybdate or ammonium dimolybdate. Tungsten is typically added to the hydrogel as ammonium metatungstate. Cobalt is added to the hydrogel in the form of dry, water-soluble cobalt nitrate, cobalt hydroxide, cobalt acetate, cobalt oxalate or cobalt oxide, with cobalt nitrate being preferred. The phosphorus-containing compound is typically added, either wet or dry, to the hydrogel in an amount ranging from about 0.17 to about 7.1 moles of phosphorus per mole of molybdenum or tungsten. Alternatively, the phosphorus-containing compound can be mixed with the dry cobalt salt or with the dry molybdenum or tungsten salt prior to addition to the hydrogel. The phosphorus-containing compound is preferably added to the hydrogel as phosphoric acid, a phosphate salt and mixtures thereof.

A preferred method of mixing the dry metal salts of cobalt and molybdenum and/or tungsten with the hydrogel consists of adding hydrogen peroxide to the mixture of dry metal salts and hydrogel in an amount ranging from about 0.1 to about 1.0 mole of hydrogen peroxide per mole of molybdenum and/or tungsten. Optionally, a suitable amine compound such as a monoethanolamine, propanolamine or ethylenediamine may be added to the mixture of dry metal salts and hydrogel in order to aid in stabilization of the mixture of the metal salts and the hydrogel.

The dry metals salts of cobalt, molybdenum and/or tungsten and the phosphorus-containing compound (if added dry) are typically added to the hydrogel in the form of finely divided particles which are generally 100 mesh or less in size. While particle size is not critical and larger particle sizes may be utilized, it is economically advantageous to use particles which are 100 mesh or less in size.

It is also within the scope of this invention to combine the two methods described above for adding the metals to the hydrogel. For example, one metal may be added to the hydrogel as a dry salt and another added in the form of a solution. Various permutations of this combination of dry salts additions and metals solutions additions would be obvious to one skilled in the art.

The temperature and pH of the step in which the metals solutions and/or the dry metal salts are mixed with the hydrogel are important variables in the preparation of hydrogel-derived catalysts which have acceptable densities and porosities. In general, higher temperatures yield lower density catalysts. The pH of the mixing step, however, is critical to the formation of catalysts having the desired properties. The mixing of the hydrogel support with the metals solution or the dry metal salts is carried out at a pH in the range between about 4.0 and about 10.0, preferably between about 4.0 and about 8.0, and a temperature in the range between about 25° C. and about 100° C., preferably between about 25° C. and about 80° C., until incorporation of the metals salts into the gel is sufficient to yield a final calcined catalyst having from about 0.1% w to about 5% w cobalt, and from 5% w to about 32% w heavy metal selected from the group cnsisting of molybdenum, tungsten and mixtures thereof, and from about 1% w to about 6% w phosphorus. Typically, the times for mixing the hydrogel and the metals will range from about 0.5 to about 2 hours. Optionally, the resulting material can be washed to remove unadsorbed metals and filtered in routine fashion.

Following the addition of the metals to the hydrogel, the resulting material is processed in one of many routine methods to produce a finished catalyst. The material may be extruded and then dried and calcined; dried, mulled with addition of water, extruded or pelletized and calcined; or partially dried, extruded or pelleted, dried more completely and calcined. Drying is accomplished by conventional means. It may be carried out by forced draft drying, vacuum drying, air drying or similar means. Drying temperatures are not critical and depend upon the particular means utilized for drying. Drying temperatures will typically range from about 50° C. to about 150° C.

In a preferred embodiment, the material is extruded and then dried. Alternatively, the material may be extruded after drying to the proper loss on ignition (LOI). However, to facilitate extrusion, organic binders and/or lubricants may be added prior to extrusion.

After drying, the material is calcined at a temperature of at least about 700° C., preferably from about 700° C. to about 900° C., to produce the finished catalyst. The material may be calcined in an oxidizing or neutral atmosphere, although air is preferred. However, if binders and/or lubricants are used the material is heated in an oxygen-containing atmosphere, preferably air, in order to burn out the binders and lubricants. Burn-out temperatures will depend on the concentration of oxygen in the burn-out atmosphere as well as the burn-out time involved. Typically, burn-out temperatures will range from about 700° C. to about 900° C. Calcining and burn-out may be combined in open or two steps. Most frequently the calcining and/or burn-out steps are combined using an oxygen-containing atmosphere.

Certain other processing steps may be incorporated into the above-described procedure without deviating from the scope and intent of this invention. For example, an intensive mixer-muller can be used to process the material prior to extrusion.

The final catalysts are found to have surface areas greater than about 225 $m^2/g$, pore volumes ranging from about 0.4 to about 1.2 cc/g and with at least about 50% of its pore volume in pores having diameters less than about 70 Å. In general, the metals contents of the final catalysts range from about 0.1% w to about 5% w cobalt, preferably from about 0.1% w to about 4% w cobalt, from about 5% w to about 18% w, preferably from about 5% w to about 14% w molybdenum, or about 8% w to about 32% w, preferably from about 18% w to about 26% w tungsten, and from about 1% w to about 6% w, preferably from about 2% w to about 4% w phosphorus.

The process of the invention can be carried out either batchwise or continuously, using a fixed catalyst bed, or a stirrer equipped reactor or other mobile catalyst contacting process as well as any other well known contacting technique. Preferred reaction conditions, e.g., temperature, pressure, flow rates, etc., vary somewhat depending upon the specific catalyst composition, the particular feed olefin, desired products, etc. The process is carried out at temperatures ranging from about 10° C. to about 350° C. and at pressures in the range of about 50 psig to about 500 psig. The disproportionation reaction is usually effected in a liquid phase in the presence of a small amount of ethylene and if desired, liquid reaction diluents are utilized. Examples of suitable diluents are hydrocarbons free from aliphatic unsaturation, such as acyclic or alicyclic alkanes of from 6 to 12 carbon atoms, i.e. hexane, isooctane and cyclohexane. Also exemplary would be monoaromatic compounds such as benzene and toluene. If the diluent is added, it is present in amounts up to 20 moles of diluent per mole of olefinic reactants.

The operable range of contact time for the process of this invention depends primarily upon the operating temperature and the activity of the catalyst, which is influenced by surface area, promoter concentration, activation temperature, etc. In general, the distribution of products is not drastically altered by variation in contact time. Shorter contact times are usually associated with higher temperatures, but, when larger amounts of higher molecular weight products are desired, a suitable combination of contact time and temperature is selected. With proper selection of conditions and contact times, very high efficiency of conversion of desired products can be obtained.

In this application, space rates are given in WHSV (weight hourly space velocity; weight of reactant feed per weight of catalyst per hour).

With a fixed bed reactor, continuous flow operation at pressures in the range of about 50 psig to about 500 psig, preferably about 150 psig to about 250 psig, with catalysts having densities ranging from about 0.5 gram per cc to about 1.0 gram per cc and surface areas greater than about 225 m$^2$/g, and at temperatures in the range of about 10° C. to about 350° C., preferably about 100° C. to about 250° C., weight hourly space velocities in the range of about 0.1 to about 10.0 parts by weight of olefinic hydrocarbon feed per part by weight of catalyst per hour are suitable. The space velocity is adjusted according to changes in density of feed due to change of pressure or temperature, and variation in reaction temperature and the activity of the catalyst. The higher space velocities in general are associated with higher reaction temperatures.

The process of the instant invention will be further described below by the following examples which are illustrative and which are not to be construed as limiting the invention.

ILLUSTRATIVE EMBODIMENTS

CATALYST PREPARATION

Catalyst A 98.3 kilograms of aluminum sulfate solution were prepared by solubilizing 11.3 kilograms of gibbsite (alpha-alumina trihydrate, 34% LOI) in 87.0 kilograms of 27% sulfuric acid at a temperature slightly above 100° C. The solution was allowed to cool to 60° C. prior to use. 75.9 kilograms of sodium aluminate solution were prepared by solubilizing 28.3 kilograms of gibbsite (alpha-alumina trihydrate, 34% LOI) in 47.6 kilograms of 36% sodium hydroxide at a temperature slightly above 115° C. This solution was also allowed to cool to 60° C. prior to use. These two solutions were metered under computer control into a precipitation vessel containing a deionized water heel (121.1 kilograms) held at 60° C., maintaining a constant pH of 7.4 and a temperature of 60° C. The precipitation duration was fixed at 15 minutes. After the precipitation step was complete excess sodium aluminate solution (8.1 kilograms) was added to the slurry to raise the pH to the desired aging pH of 10.6. Total solution quantities used: acid-44.3 kilograms, base-35.1 kilograms. The slurry was aged for one hour at the elevated pH. The slurry was then filtered in a single step on a 1'×10' horizontal belt vacuum filter and washed with deionized water. The resulting alumina hydrogel generally had a water content between 75% and 90%, basis dry weight of alumina.

Into a vessel equipped with a high speed stirrer were added a portion of alumina hydrogel prepared during a 15 minute precipitation (4000 g, 85.0% LOI-600 g dry weight basis), cobalt nitrate hexahydrate (18.0 g), 85% phosphoric acid (108.5 g) and ammonium heptamolybdate (67.2 g). The mixture was stirred vigorously to "liquefy" the hydrogel. After reaction for 1.5 hours at 25° C. the catalyst hydrogel slurry was passed through a Gaulin Model 15M Lab Homogenizer using a pressure dro of 6000 psi. The stiffened material from this homogenization step was extruded using a small manifold and nozzle system designed in-house for the homogenizer system. Drying of the extrudate at 130° C. was followed by calcination at 725° C. for two hours. The properties of the catalyst are listed in Table I.

Calalyst B

Catalyst B was prepared in a manner similar to Catalyst A except that the catalyst was calcined at a temperature of 525° C. The properties of the catalyst are listed in Table I.

Catalyst C

Catalyst C was prepared in a manner similar to Catalyst A except that the preparation temperature was 75° C. and the final calcined catalyst contained 0.5% w phosphorus. The properties of the catalyst are listed in Table I.

Catalyst D

Catalyst D was prepared using a conventional dry pore volume impregnation technique. A solution suitable for impregnating 75 grams of calcined alumina support with a pore volume of 0.69 cc/g was prepared as folows. An impregnation solution was made by combining 5.78 grams of cobalt nitrate, 12.86 grams of ammonium dimolybdate and enough 24% aqueous ammonia to bring the solution to a total volume of 51 milliliters. After adding the entire solution of the alumina support in several small portions with intermediate agitations, the impregnated support was dried overnight at 150° C. and calcined in air for 2 hours at 450° C. The properties of the catalyst are listed in Table I.

CATALYST TESTING

Catalysts A, B, C and D were each tested utilizing the following procedure. For testing, 4 grams of undiluted catalyst sized 16-45 mesh were charged to a 0.60" ID stainless steel reactor equipped with a 0.19" OD thermowell. The catalyst was activated by heating in flowing air at a rate of 50 cm$^3$/minute for 1.5 hours, while the temperature was ramped from ambient temperature to 975° F. The catalyst was held at 975° F. for 4 hours under flowing air, followed by flowing N$_2$ at 50 cm$^3$/minute for an additional 12 hours. After activation, the catalyst was cooled under N$_2$ to reaction temperature, 150° F., and equilibrium isomerized decenes were introduced as feed.

Disproportionation rates were measured by monitoring the disappearance of C$_{10}$ in the reaction product. The reaction temperature was held constant at 150° F. for the 6.5 hour catalyst test, while feed weight hourly space velocity (WHSV) was adjusted twice during the run. Measurements of C$_{10}$ conversion were made after 1.5 hours at 32 WHSV, 2.0 hours at 24 WHSV and 3 hours at 16 WHSV. The slope of the line obtained from plotting C$_{10}$ remaining versus 1/WHSV then yielded the reaction rate. Disproportionation rates for the hydrogel catalysts are reported relative to the conventionally prepared impregnated catalyst (Catalyst D). The results of the catalyst testing are presented in Table II.

As mentioned previously, hydrogel catalysts prepared by the process of the instant invention have improved disproportionation activities relative to conventionally prepared catalysts. The disproportionation activities in Table II are reported relative to Catalyst D, the conventionally prepared impregnated catalyst. Catalysts yielding higher disproportionation rates are shown by having values greater than 1.00. It is evident from these data that hydrogel-derived Catalyst A demonstrates an enhanced disproportionation rate on a volumetric basis relative to Catalyst D. It is also evident from these data that Catalysts B and C, which were not prepared according to the invention, have lower disproportionation rates than the conventionally prepared impregnated catalyst.

TABLE I

Catalyst Properties

| Catalyst | A | B | C | D |
|---|---|---|---|---|
| % wt. Molybdenum[a] | 5.0 | 5.0 | 5.0 | 8.1 |
| % wt. Cobalt[b] | 0.5 | 0.5 | 0.5 | 3.2 |
| % wt. Phosphorus[c] | 4.0 | 4.0 | 0.5 | 0.0 |
| Calcination Temperature | 725 | 525 | 725 | 450 |
| Surface Area[d] m²/gm | 347 | 424 | 237 | 295 |
| Pore Volume[e] cc/gm | 0.77 | 0.81 | 0.48 | 0.51 |
| Compacted Bulk Density[f] gm/cc | 0.49 | 0.57 | 0.78 | 0.66 |
| Hg Pore Size Distribution[g] | | | | |
| <50 Å | 8.5 | 33.9 | 5.1 | 4.7 |
| 50–70 Å | 50.4 | 38.7 | 84.8 | 39.5 |
| 70–100 Å | 29.3 | 14.4 | 7.8 | 33.3 |
| 100–150 Å | 7.2 | 6.2 | 1.2 | 9.8 |
| 150–350 Å | 3.7 | 4.9 | 1.0 | 7.5 |
| >350 Å | 0.9 | 1.9 | 0.0 | 5.2 |

[a] Weight percent determined by neutron activation analysis or atomic absorption spectroscopy.
[b] Weight percent determined by neutron activation analysis or atomic absorption spectroscopy.
[c] Weight percent determined by neutron activation analysis or atomic absorption spectroscopy.
[d] BET, by nitrogen adsorption/desorption, Micromeritics Digisorb 2500 Instrument.
[e] By nitrogen adsorption, Micromeritics Digisorb 2500 Instrument.
[f] 209 cc volume fully settled in a graduated cup and weighed.
[g] Determined by mercury intrusion, to 60,000 psi using a Micromeritics Autopore 9210, using a 130° contact angle and 0.473 N/m surface tension of mercury. Numbers listed are percent pore volume.

TABLE II

Catalyst Test Results

| Catalyst | A | B | C | D |
|---|---|---|---|---|
| $C_{10}$ Feed | Iso. $C_{10}$ | Iso. $C_{10}$ | Iso. $C_{10}$ | Iso. $C_{10}$ |
| Reaction Temperature, °F. | 150 | 150 | 150 | 150 |
| Disproportionation Activity | | | | |
| Catalyst Weight, gm | 4.0 | 4.0 | 4.0 | 4.0 |
| Catalyst Volume, cc | 8.1 | 7.1 | 5.1 | 5.1 |
| Rate, g/g/hr | 14.08 | 0.81 | 1.41 | 1.59 |
| Relative Rate | | | | |
| Basis Volume | 5.58 | 0.37 | 0.89 | 1.00 |

We claim as our invention:

1. A process for the disproportionation of olefinic hydrocarbons having carbon numbers ranging from $C_2$ to about $C_{100}$ which comprises contacting said olefinic hydrocarbons at disproportionation conditions with a catalyst prepared by a process which comprises:
   (a) preparing an alumina hydrogel having a sufficient water content to provide a hydrogel which is thixotropic,
   (b) mixing said alumina hydrogel with cobalt, a heavy metal selected from the group consisting of molybdenum, tungsten and mixtures thereof, and a phosphorus-containing compound in an amount of from about 0.17 to about 7.1 moles of phosphorus per mole of heavy metal at a pH in the range between about 4.0 and about 10.0 and a temperature in the range between about 25° C. and about 100° C. until adsorption of the cobalt, heavy metal and phosphorus-containing compound onto the gel is sufficient to yield a final catalyst having from about 0.1% by weight to about 5% by weight cobalt from about 5% by weight to about 32% by weight heavy metal, and from about 1% by weight to about 6% by weight phosphorus,
   (c) extruding the product of step (b), and
   (d) calcining the product of step (c) at a temperature of at least about 700° C.

2. The process of claim 1 wherein said alumina hydrogel has a water content greater than about 70%, basis dry weight of alumina.

3. The process of claim 2 wherein said alumina hydrogel has a water content in the range of from about 70% to about 95%, basis dry weight of alumina.

4. The process of claim 1 wherein in step (a), a phosphorus-containing compound is added in an amount ranging from about 0.02 to about 0.60 moles of phosphorus per mole of aluminum.

5. The process of claim 4 wherein said phosphorus-containing compound is selected from the group consisting of phosphoric acid, a phosphate salt and mixtures thereof.

6. The process of claim 1 wherein said heavy metal is molybdenum.

7. The process of claim 6 wherein said catalyst contains from about 0.1% by weight to about 4% by weight cobalt and from about 5% by weight to about 18% by weight molybdenum.

8. The process of claim 1 wherein said catalyst contains from about 2% by weight to about 4% by weight phosphorus.

9. The process of claim 1 wherein said phosphorus-containing compound is selected from the group consisting of phosphoric acid, a phosphate salt and mixtures thereof.

10. The process of claim 1 wherein the calcination is carried out at a temperature in the range of from about 700° C. to about 900° C.

11. The process of claim 1 wherein said catalyst has a surface area greater than about 225 m²/g and at least about 50% of its pore volume in pores having diameters less than about 70 Å.

12. The process of claim 1 wherein said olefinic hydrocarbons have carbon numbers ranging from $C_2$ to about $C_{60}$.

13. The process of claim 1 wherein said disproportionation conditions include a temperature of from about 10° C. to about 350° C. and a pressure of from about 50 psig to about 500 psig.

14. A process for the disproportionation of olefinic hydrocarbons having carbon numbers ranging from $C_2$ to about $C_{100}$ which comprises contacting said olefinic hydrocarbons at disproportionation conditions with a catalyst prepared by a process which comprises:
   (a) preparing an alumina hydrogel having a sufficient water content to provide a hydrogel which is thixotropic,
   (b) mixing said alumina hydrogel with a solution containing solubilized salts of cobalt, a heavy metal selected from the group consisting of molybdenum, tungsten and mixtures thereof and a phosphorus-containing compound in an amount of from about 0.17 to about 7.1 moles of phosphorus per mole of heavy metal, at a pH in the range between about 4.0 and about 10.0 and a temperature in the range between about 25° C. and about 100° C. until adsorption of the cobalt, heavy metal and phosphorus-containing compound onto the gel is sufficient to yield a final catalyst having from about 0.1% by weight to about 5% by weight cobalt, from about 5% by weight to about 32% by weight heavy metal, and from about 1% by weight to about 6% by weight phosphorus, (c) extruding the product of step (b), and (d) calcining the product of step (c) at a temperature of at least about 700° C.

15. The process of claim 14 wherein said alumina hydrogel has a water content greater than about 70%, basis dry weight of alumina.

16. The process of claim 15 wherein said alumina hydrogel has a water content in the range of from about 70% to about 95%, basis dry weight of alumina.

17. The process of claim 14 wherein in step (a), a phosphorus-containing compound is added in an amount ranging from about 0.02 to about 0.60 moles of phosphorus per mole of aluminum.

18. The process of claim 17 wherein said phosphorus-containing compound is selected from the group consisting of phosphoric acid, a phosphate salt and mixtures thereof.

19. The process of claim 14 wherein said heavy metal is molybdenum.

20. The process of claim 19 wherein said catalyst contains from about 0.1% by weight to about 4% by weight cobalt and from about 5% by weight to about 18% by weight molybdenum.

21. The process of claim 14 wherein said catalyst contains from about 2% by weight to about 4% by weight phosphorus.

22. The process of claim 14 wherein said phosphorus-containing compound is selected from the group consisting of phosphoric acid, a phosphate salt and mixtures thereof.

23. The process of claim 14 wherein the calcination is carried out at a temperature in the range of from about 700° C. to about 900° C.

24. The process of claim 14 wherein said catalyst has a surface area greater than about 225 m²/g and at least about 50% of its pore volume in pores having diameters less than about 70 Å.

25. The process of claim 14 wherein said olefinic hydrocarbons have carbon numbers ranging from $C_2$ to about $C_{60}$.

26. The process of claim 14 wherein said disproportionation conditions include a temperature of from about 10° C. to about 350° C. and a pressure of from about 50 psig to about 500 psig.

27. A process for the disproportionation of olefinic hydrocarbons having carbon numbers ranging from $C_2$ to about $C_{100}$ which comprises contacting said olefinic hydrocarbons at disproportionation conditions with a catalyst prepared by a process which comprises:

(a) preparing an alumina hydrogel having a sufficient water content to provide a hydrogel which is thixotropic, (b) mixing said alumina hydrogel the precipitate with dry, water-soluble salts of cobalt, a heavy metal selected from the group consisting of molybdenum, tungsten and mixtures thereof, and a phosphorus-containing compound in an amount of from about 0.17 to about 7.1 moles of phosphorus per mole of heavy metal at a pH in the range between about 4.0 and about 10.0 and a temperature in the range between about 25° C. and about 100° C. until adsorption of the cobalt, heavy metal and phosphorus-containing compound onto the gel is sufficient to yield a final catalyst having from about 0.1% by weight to about 5% by weight cobalt, from about 5% by weight to about 32% by weight heavy metal, and from about 1% by weight to about 6% by weight phosphorus, (c) extruding the product of step (b), and (d) calcining the product of step (c) at a temperature of at least about 700° C.

28. The process of claim 27 wherein said alumina hydrogel has a water content greater than about 70%, basis dry weight of alumina.

29. The process of claim 28 wherein said alumina hydrogel has a water content between about 70% and about 95%, basis dry weight of alumina.

30. The process of claim 27 wherein in step (a), a phosphorus-containing compound is added in an amount ranging from about 0.02 to about 0.60 moles of phosphorus per mole of aluminum.

31. The process of claim 30 wherein said phosphorus-containing compound is selected from the group consisting of phosphoric acid, a phosphate salt and mixtures thereof.

32. The process of claim 27 wherein said heavy metal is molybdenum.

33. The process of claim 32 wherein said catalyst contains from about 0.1% by weight to about 4% by weight cobalt and from about 8% by weight to about 18% by weight molybdenum.

34. The process of claim 27 wherein said catalyst contains from about 2% by weight to about 4% by weight phosphorus.

35. The process of claim 27 wherein said phosphorus-containing compound is selected from the group consisting of phosphoric acid, a phosphate salt and mixtures thereof.

36. The process of claim 27 wherein the calcination is carried out at a temperature in the range of from about 700° C. to about 900° C.

37. The process of claim 27 wherein said catalyst has a surface area greater than about 225 m²/g and at least about 50% of its pore volume in pores having diameters less than about 70 Å.

38. The process of claim 27 wherein said olefinic hydrocarbons have carbon numbers ranging from about $C_2$ to about $C_{60}$.

39. The process of claim 27 wherein said disproportionation conditions include a temperature of from about 10° C. to about 350° C. and a pressure of from about 50 psig to about 500 psig.

40. A process for the disproportionation of olefinic hydrocarbons having carbon numbers ranging from $C_2$ to about $C_{100}$ which comprises contacting said olefinic hydrocarbons at disproportionation conditions with a catalyst prepared by a process which comprises:

(a) preparing an alumina hydrogel having a sufficient water content to provide a hydrogel which is thixotropic, (b) mixing a dry water-soluble salt of a heavy metal selected from the group consisting of molybdenum, tungsten and mixtures thereof, and a mixture of a dry, water-soluble cobalt salts and a phosphorus-containing compound in an amount of from about 0.17 to about 7.1 moles of phosphorus per mole of heavy metal with said alumina hydrogel at a pH in the range between about 4.0 and about 10.0 and a temperature in the range between about 25° C. and about 100° C. until adsorption of the heavy metal, cobalt and phosphorus-containing compound onto the gel is sufficient to yield a final catalyst having from about 0.1% by weight to about 5% by weight cobalt, from about 5% by weight to about 32% by weight heavy metal, and from about 1% by weight to about 6% by weight phosphorus, (c) extruding the product of step (b), and (d) calcining the product of step (c) at a temperature of at least about 700° C.

41. The process of claim 40 wherein said alumina hydrogel has a water content greater than about 70%, basis dry weight of alumina.

42. The process of claim 41 wherein said alumina hydrogel has a water content in the range of from about 70% to about 95%, basis dry weight of alumina.

43. The process of claim 40 wherein in step (a), a phosphorus-containing compound is added in an amount ranging from about 0.02 to about 0.60 moles of phosphorus per mole of aluminum.

44. The process of claim 43 wherein said phosphorus-containing compound is selected from the group consisting of phosphoric acid, a phosphate salt and mixtures thereof.

45. The process of claim 40 wherein said salt of said heavy metal is a molybdenum salt.

46. The process of claim 45 wherein said catalyst contains from about 0.1% by weight to about 4% by weight cobalt and from about 5% by weight to about 18% by weight molybdenum.

47. The process of claim 40 wherein said catalyst contains from about 2% by weight to about 4% by weight phosphorus.

48. The process of claim 40 wherein said phosphorus-containing compound is selected from the group consisting of phosphoric acid, a phosphate salt and mixtures thereof.

49. The process of claim 40 wherein the calcination is carried out at a temperature in the range of from about 700° C. to about 900° C.

50. The process of claim 40 wherein said catalyst has a surface area greater than about 225 $m^2/g$ and at least about 50% of its pore volume in pores having diameters less than about 70 Å.

51. The process of claim 40 wherein said olefinic hydrocarbons have carbon numbers ranging from $C_2$ to about $C_{60}$.

52. The process of claim 40 wherein said disproportionation conditions include a temperature of from about 10° C. to about 350° C. and a pressure of from about 50 psig to about 500 psig.

* * * * *